US009986943B2

(12) United States Patent
Zakaria et al.

(10) Patent No.: US 9,986,943 B2
(45) Date of Patent: Jun. 5, 2018

(54) SAFETY NEEDLE BLOOD SAMPLING DEVICES AND RELATED METHODS

(71) Applicant: B. BRAUN MELSUNGEN AG, Melsungen (DE)

(72) Inventors: Mohd Zairizal Bin Zakaria, Penang (MY); Hwa Loon Chan, Penang (MY); Teng Sun Teoh, Penang (MY); Ai-Mei Tan, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 291 days.

(21) Appl. No.: 14/311,024

(22) Filed: Jun. 20, 2014

(65) Prior Publication Data

US 2015/0366496 A1 Dec. 24, 2015

(51) Int. Cl.
*A61B 5/00* (2006.01)
*A61B 5/15* (2006.01)
*A61B 5/154* (2006.01)

(52) U.S. Cl.
CPC .... *A61B 5/150274* (2013.01); *A61B 5/15003* (2013.01); *A61B 5/154* (2013.01); *A61B 5/150389* (2013.01); *A61B 5/150473* (2013.01); *A61B 5/150572* (2013.01); *A61B 5/150648* (2013.01); *A61B 5/150717* (2013.01); *A61B 5/150732* (2013.01); *Y10T 29/49865* (2015.01)

(58) Field of Classification Search
CPC .. A61B 5/1405; A61B 5/1438; A61B 5/15003
USPC ...................................................... 600/576
See application file for complete search history.

(56) References Cited

U.S. PATENT DOCUMENTS

| 5,222,947 | A | 6/1993 | D'Amico | |
|---|---|---|---|---|
| 6,869,415 | B2 | 3/2005 | Asbaghi | |
| 6,984,223 | B2 | 1/2006 | Newby et al. | |
| 7,357,783 | B2 | 4/2008 | Millerd | |
| 8,162,882 | B2 | 4/2012 | Rubinstein et al. | |
| RE43,473 | E | 6/2012 | Newby et al. | |
| 2003/0093009 | A1* | 5/2003 | Newby ................ | A61B 5/1438 600/576 |
| 2003/0181871 | A1* | 9/2003 | Wilkinson ............ | A61M 5/178 604/263 |
| 2004/0210197 | A1* | 10/2004 | Conway ............... | A61B 5/1444 604/198 |
| 2004/0236287 | A1 | 11/2004 | Swenson et al. | |
| 2005/0119627 | A1* | 6/2005 | Crawford ............ | A61M 5/3243 604/263 |

(Continued)

FOREIGN PATENT DOCUMENTS

CN          102599920 A       7/2012

*Primary Examiner* — Daniel Cerioni
(74) *Attorney, Agent, or Firm* — Klein, O'Neill & Singh, LLP

(57) ABSTRACT

Blood collection assemblies with safety features are disclosed. The assemblies have a housing for receiving a vacutainer, which has a septum that penetrates a sharp needle tip. The disclosed assemblies further have a shield for covering the other end of the needle following use to prevent accidental contact with the distal needle tip. The shield is spring loaded so that the spring force moves the shield over the needle. The shield can be secured or held in an initial position and allowed to move to cover the needle upon actuation or activation of an activator unit.

13 Claims, 10 Drawing Sheets

(56) References Cited

U.S. PATENT DOCUMENTS

2008/0319346 A1* 12/2008 Crawford ............ A61B 5/1422
  600/577
2011/0166476 A1  7/2011 Crawford et al.
2012/0150125 A1  6/2012 Karlsson et al.

* cited by examiner

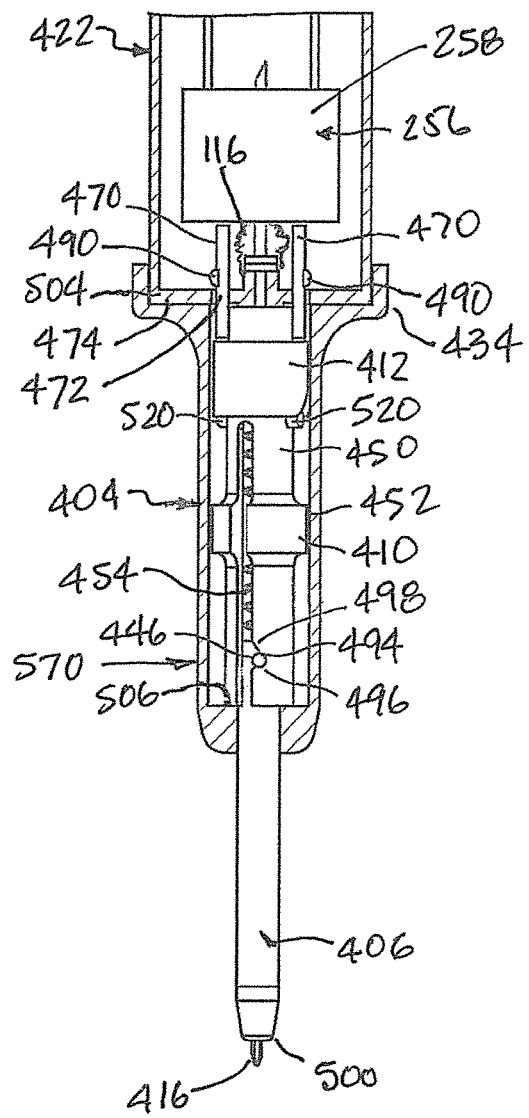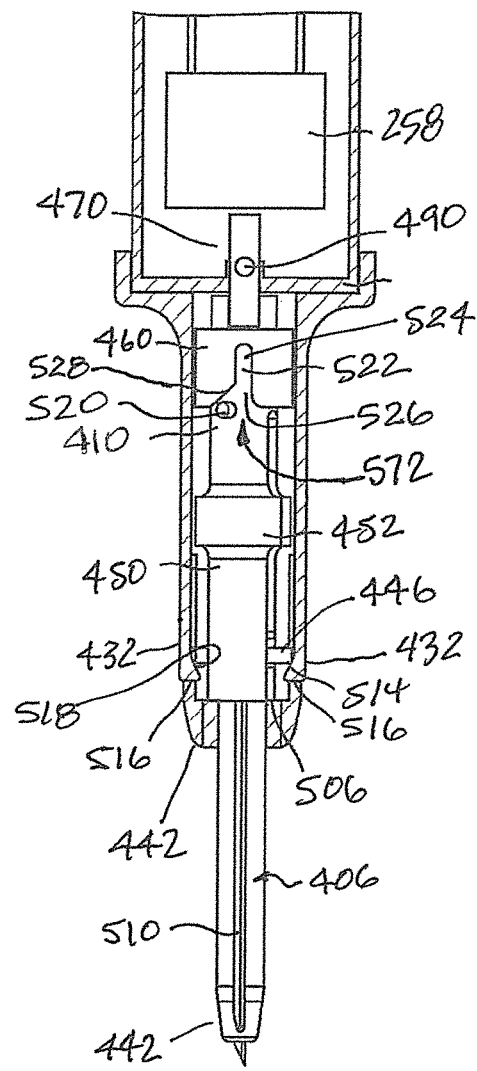

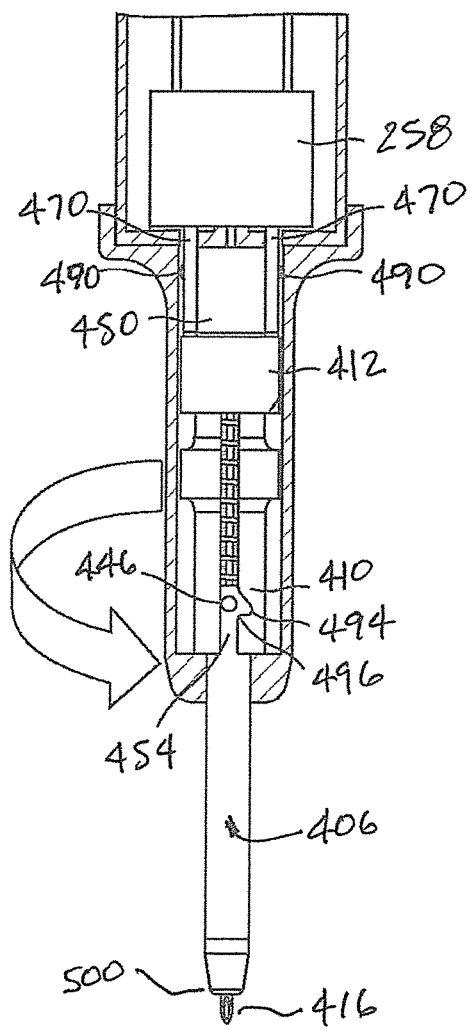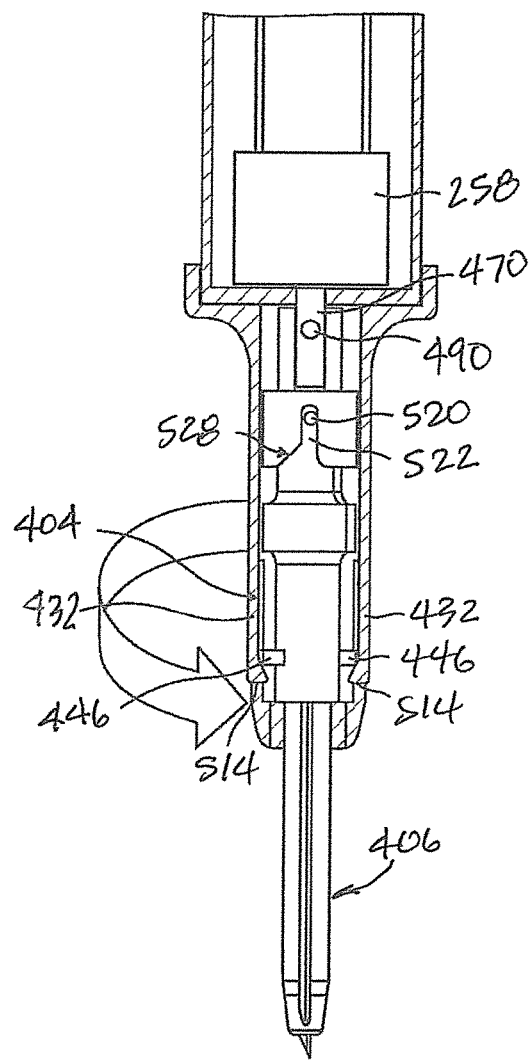

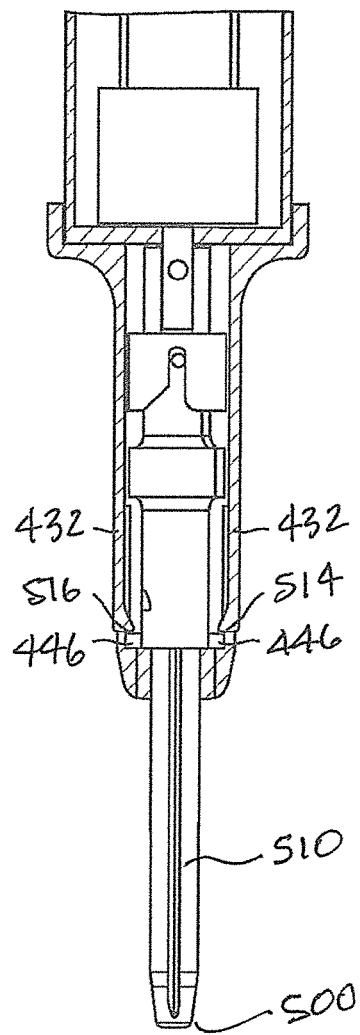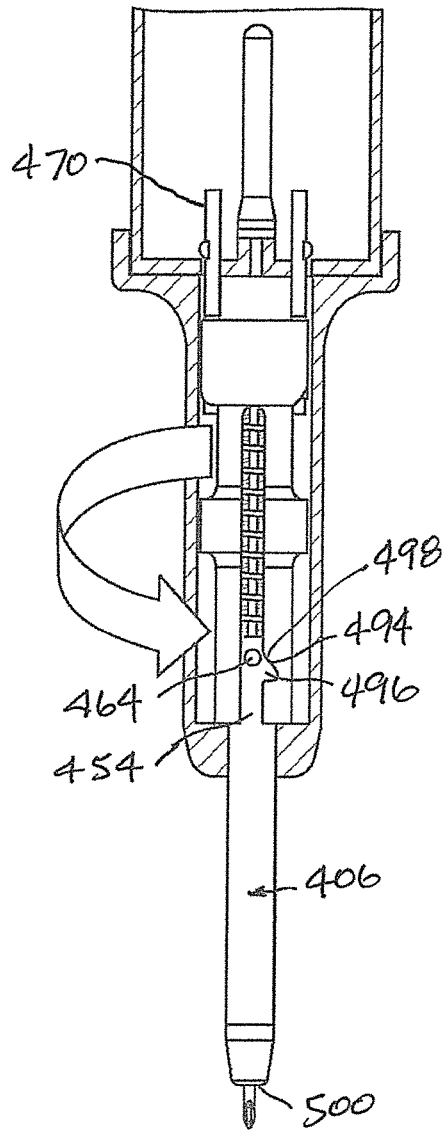
FIG. 11
FIG. 12

SAFETY NEEDLE BLOOD SAMPLING DEVICES AND RELATED METHODS

FIELD OF ART

This invention relates generally to blood sampling or collection devices, systems and methods for taking a blood sample from a patient using a blood sample vial, also known as a vacutainer. More specifically, aspects of the present disclosure relate to blood sampling systems or assemblies including a needle safety shield, methods for using the blood sampling systems and methods for making such systems.

BACKGROUND

Medical care of individuals requires the widespread use of needles for taking blood samples, intravenous drug delivery, and the introduction or removal of other fluids via cannula, needles, or syringes, among other things. In the current context, the use of hypodermic needles to take blood samples has become commonplace in medicine, science, veterinary medicine, and biotechnology. The use of a hypodermic needle typically involves first inserting a needle into the patient, withdrawing a substance as required, and then removing the needle from the patient. In most applications, the withdrawn and contaminated needle must be handled carefully during disposal to avoid unintended needle stick injury.

To help prevent health care workers from becoming injured, safety means such as guards and shields have been developed to block the tip of these needles after use. Indeed, needle stick protection for medical professionals has become of particular importance in recent years because of the prevalence of potentially fatal infectious diseases, such as, for example, Acquired Immune Deficiency Syndrome (AIDS) and hepatitis that can be transmitted by the exchange of bodily fluids through inadvertent wounds caused by accidental needle tip pricks after withdrawal from infected patients. Accordingly, many kinds of needle protection devices are available for providing post injection needle stick protection.

Devices which have been introduced to provide added protection against punctures by used needles fall into three basic categories, those which hide the withdrawn needle within a needle shield launched via a needle shield launching mechanism, those which require placement of a separate needle guard, and those which include a sliding shield which must be manually pushed along the needle shaft and over the tip of the used needle. Most of these needle guards are cumbersome and interfere with a single-handed procedure, and or require additional complicated pieces to attach the needle guard to the needle tip.

SUMMARY

A safety needle blood sampling assembly or device is disclosed. In an embodiment, the device comprises a housing comprising a first housing section and a second housing section having an interior space; a needle passing through the housing and having a needle shaft extending at least partially in the first housing section for cannulation and the second housing section for connection to a sampling vial; an activator unit disposed in the interior space of the housing; said activator unit comprising an activator base and an activator lever and wherein at least one of the activator base and the activator lever is rotatable and wherein the needle shaft passes through the activator base; a protective shield having a bore and being urged by a helical spring disposed at least partially inside the first housing section. In a particular example, the protective shield is engaged by the activator unit to maintain the spring in a compressed state in a ready to use position with a first needle tip exposed distal of the protective shield.

The safety needle blood sampling device wherein the first housing section can snap fit around an outside surface of the second housing section.

The safety needle blood sampling device wherein the activator lever can comprise a pivotable pin attached to a channel formed in the activator base.

The safety needle blood sampling device wherein the activator lever can include a hook end that hooks into a receptacle on the protective shield in the ready to use position.

The safety needle blood sampling device wherein the activation base can have at least one channel extending parallel to the needle.

The safety needle blood sampling device wherein the protective shield can comprise a stub and wherein the stub engages a catchment on the activator base in the ready to use position.

The safety needle blood sampling device wherein the activator lever can have a leg that extends through bore on an end wall of the second housing section.

The present disclosure further describes a safety needle blood sampling device comprising a housing comprising a first housing section and a second housing section having an interior space; a needle passing through the housing and having a needle shaft extending at least partially in the first housing section for cannulation and the second housing section for connection to a sampling vial; an activator unit disposed in the interior space of the housing; said activator unit comprising an activator base and an activator lever and wherein the activator lever has at least one leg located in the second housing section for contacting the sampling vial when the sampling vial is located in the second housing section and wherein the needle shaft passes through the activator base; a protective shield having a body defining bore and being urged by a helical spring disposed at least partially inside the first housing section, said protective shield comprising a tapered nose section; and wherein the protective shield is engaged by the activator base or the activator lever to maintain the spring in a compressed state in a ready to use position with a first needle tip exposed distal of the protective shield.

The safety needle blood sampling device with the at least one leg wherein the first housing section can snap fit around an outside surface of the second housing section.

The safety needle blood sampling device with the at least one leg wherein the activator lever can comprise a pivotable pin attached to a channel formed in the activator base and the at least one leg defines a push end.

The safety needle blood sampling device with the at least one leg, wherein the activator lever can have a hook end that hooks into a receptacle on the protective shield in the ready to use position.

The safety needle blood sampling device with the at least one leg, wherein the activation base can have at least one channel extending parallel to the needle.

The safety needle blood sampling device with the at least one leg, wherein the protective shield can comprise a stub and wherein the stub engages a catchment on the activator base in the ready to use position.

The safety needle blood sampling device with the at least one leg, wherein the activator lever can have a cylinder end comprising a catchment for engaging a stub on the activator lever.

A still further aspect of the present disclosure is a method of manufacturing a needle blood sampling device. In accordance with aspects of the present disclosure, the method comprising the steps of forming a multi-part housing comprising a first housing section and a second housing section having an interior space; placing a needle through housing and having a needle shaft extending at least partially through the first housing section for cannulation and the second housing section for connection to a sampling vial; placing an activator unit in the interior space of the housing; said activator unit comprising an activator base and an activator lever and wherein the activator lever has at least one leg located in the second housing section for contacting the sampling vial when the sampling vial is located in the second housing section and wherein the needle shaft passes through the activator base; placing a protective shield having a body defining bore and being urged by a helical spring at least partially inside the first housing section, said protective shield comprising a tapered nose section; and engaging the protective shield to the activator base or to the activator lever to maintain the spring in a compressed state in a ready to use position with a first needle tip exposed distal of the protective shield.

The method wherein the forming step can comprise inserting an end of the second housing section into a bore of the first housing section in a snap fit arrangement.

The method wherein the activator lever can comprise a pivotable pin attached to a channel formed in the activator base and the at least one leg defines a push end.

The method wherein the activator lever can have a hook end that hooks into a receptacle on the protective shield in the ready to use position.

The method wherein the activation base can have at least one channel extending parallel to the needle.

The method wherein the protective shield can comprise a stub and wherein the stub engages a catchment on the activator base in the ready to use position.

The method wherein the activator lever can have a cylinder end comprising a catchment for engaging a stub on the activator lever.

Another feature of the present disclosure is a passive safety needle blood sampling device. The device comprises: a housing comprising a needle holder comprising a base with a flange, a distal end wall, and a body wall having an interior diameter defining an interior cavity and an exterior diameter; said body wall defining a lengthwise longitudinal axis having an open proximal end; a cap having wall structure comprising an exterior surface, an interior surface defining an interior cavity, a distal end, and a proximal end connected to a distal end of the housing; at least one catch formed upon the cap, the at least one catch comprising a rectangular section extending distally of a connection point on the cap and comprising a triangular shaped section comprising a portion extending partially radially inward into the interior cavity of the cap; a double tipped needle comprising a distal end section and a proximal end section, the distal end section extending distally of the distal end of the cap and the proximal end section of the needle extending into the interior cavity of the housing and having a deformable sleeve mounted there-over forming a multi-sampling Luer adaptor; a safety shield comprising a first elongated section surrounding at least a portion of the distal end section of the needle and a second enlarged section comprising an interior having a shoulder, an exterior, and a flange at a proximal end thereof; an activator comprising a body wall structure having a distal end with a distal end wall and a proximal end with an opening through which the multi-sampling Luer adaptor extends; said activator comprising two spaced apart legs with each leg comprising a hook end and extending through the distal end wall of the housing and gripping the flange on the second enlarged section of the safety shield such that the distal end wall of the activator is spaced from the distal end wall of the housing by a starting gap in a ready to use position; a helical spring positioned in the interior of the second enlarged section of the safety shield and compressed by the shoulder of the second enlarged section and the distal end wall of the housing; the spring being held compressed by the hook ends of the two legs gripping the flange on the safety shield; a ramped section at the distal end wall of the housing in abutting contact with the two spaced apart arms; wherein the activator is movable distally when a sampling vial is inserted into the open proximal end of the housing and pushing on the activator in a distal direction, whereupon the two legs deflect by the ramped section at the distal end wall of the housing to be further spaced from one another to release the flange on the safety shield from the gripping by the two hook ends; and wherein the distal end wall of the activator is spaced from the distal end wall of the housing by an activated gap in a protective position, which is less than the starting gap, when the two spaced apart arms no longer grip the flange on the safety shield.

The present disclosure further describes an alternative passive safety needle blood sampling device, comprising: a double tipped needle comprising a distal end comprising a distal tip and a proximal end, comprising a proximal tip having a deformable sleeve mounted there-over forming a multi-sampling Luer adaptor; said needle having a lengthwise axis; a housing sized and shaped to receive a blood sampling vial and comprising a base comprising a flange and having a hollow member disposed therein and fixed in relative relation therewith; said hollow member comprising an end wall comprising a plurality of openings; a protective shield comprising at least two deflectable legs each comprising a hook end coaxially disposed with the hollow member and having the two hook ends engaged with two of the openings on the hollow member; a helical spring compressed on one end by the protective shield and another end by the end wall of the hollow cylinder; an activator comprising a base having a central opening and two spaced apart leg elements each comprising a hook end and wherein the two spaced apart leg elements extending through a respective opening on the end wall of the hollow cylinder and the two hook ends gripping the hollow cylinder such that the base of the activator is spaced from the end wall of the hollow cylinder by a starting gap in a ready to use position; and wherein when the activator is moved distally by a blood sampling vial, the two leg elements move to press against the two hook ends on the two deflectable legs of the protective shield to release the helical spring; and wherein the base of the activator is spaced from the end wall of the hollow cylinder by an activated gap, which is less than the starting gap, when the two leg elements move to press against the two hook ends on the two deflectable legs of the protective shield.

BRIEF DESCRIPTION OF THE DRAWINGS

These and other features and advantages of the present device, system, and method will become appreciated as the same becomes better understood with reference to the specification, claims and appended drawings wherein:

FIG. 7 shows a close up cross sectional side view of the assembled assembly of FIG. 6 in a ready position.

FIG. 8 shows the assembly of FIG. 7 turned 90 degrees.

FIG. 9 shows the assembly of FIG. 8 in an activated position with a blood sample vial inserted into the second housing.

FIG. 10 shows the view of FIG. 9 rotated 90 degrees.

FIG. 11 shows the embodiment of FIG. 6 in a protected position.

FIG. 12 shows the embodiment of FIG. 6 activated using an alternative activation mode.

DETAILED DESCRIPTION

The detailed description set forth below in connection with the appended drawings is intended as a description of the presently preferred embodiments of safety needle blood sampling devices, systems, and methods provided in accordance with aspects of the present disclosure and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
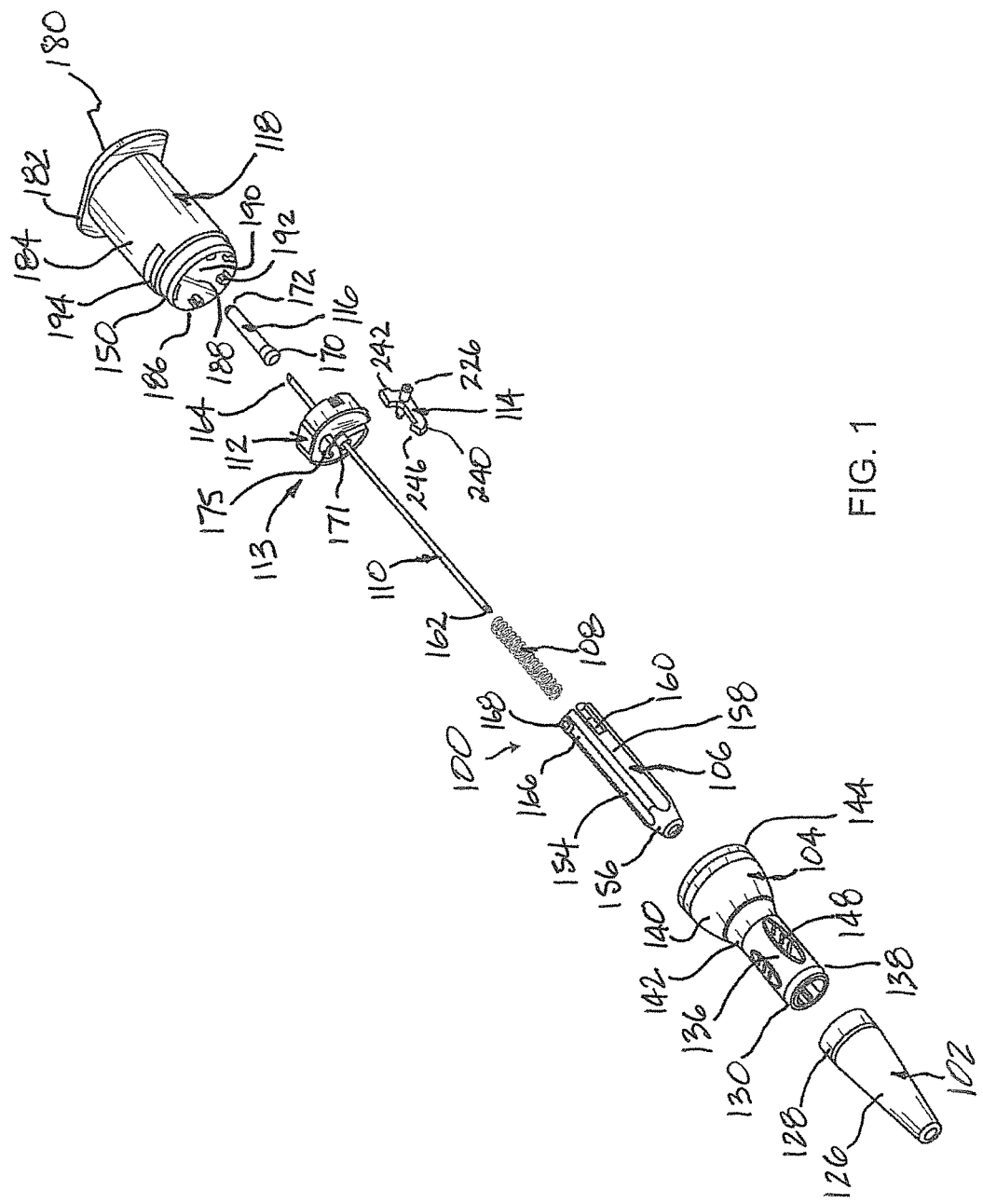
FIG. 1 shows an exploded perspective view of a passive needle blood sampling assembly in accordance with aspects of the present disclosure.

With reference now to FIG. 1, an exploded view of a safety needle blood sample or blood collection assembly 100 is shown. The assembly may also be referred to as a blood sample or blood collection device. As shown, the assembly 100 comprises a removable cap 102, a first housing 104, a protective shield 106, which may also be referred to as a sleeve or protective guard, a biasing spring 108, which can be a helical spring, a needle 110, an activator unit 113 comprising an activator base 112 and an activator lever 114, a multi-sampling Luer adaptor (MSLA) 116, and a second housing 118. The protective shield 106 is configured to automatically cover the needle 110 upon retraction of the needle from a patient or a subject without any added step and therefore may be referred to as a passive safety needle blood sampling device or assembly. In other examples, a separate triggering step is provided following retraction of the needle from the patient before the shield 106 is movable over the needle to cover the needle tip making it an optional active safety device. When assembled, the second housing 118 is sized and shaped to receive a vacuum tube and the device 100 may be used to draw a blood sample into the vacuum tube. As used herein, the terms first, second, third, etc. are used as names to designate between different components only and not to structurally limit the different components unless the context indicates otherwise.

As shown, the cap 102 comprises a frustoconical body 126 with a cylindrical lower section 128 for engaging the nose section 130 of the first housing 104. The cap 102 is for packaging and transporting and is removable from the first housing 104 before use. The cap as well as the various components discussed herein, excluding the spring and the needle, may be made from plastic injection using conventional plastics.

The first housing 104 comprises a body 136 comprising a bore, a first end 138 having the nose section 130 for engaging the cap 102, and a second end 140 with a transition section 142 therebetween. The nose section 130 is open or has an opening for the shield to slide therein. As shown, the first end 138 is generally cylindrical with a first outside diameter and the second end is generally bulb shape or tear drop shape having a second outside diameter, which is larger than the first outside diameter. A generally cylindrical base section 144 is provided for engaging the nose section 150 of the second housing 118, as further discussed below. Optional gripping features 148 may be provided on the first end 138, which also gives the assembly an aesthetic appeal. The gripping sections may embody raised projections unitarily formed with the first housing section 104 or may embody inlaid elastomeric sheets. In one example, four spaced apart gripping sections 148 are incorporated. However, there may be more or less than four gripping sections.

The protective shield 106 has an elongated body 154 with a bore, a tapered nose section 156 with an open distal end, and a multi-sided main body section 158 having an open proximal end. In other examples, the main body 154 is generally cylindrical. Two or more cut-outs 160 are provided near the proximal end of the main body section to form leaf springs 166 that can deflect. The length and size of the cut-outs can be sized and shaped to control the amount of deflection of the leaf springs. As shown, each leaf spring 166 has a flared section 168, such as a projection, a raised bump, or a curved end, for interacting with latching surfaces in the first housing 104, as further discussed below.

Figure 3:
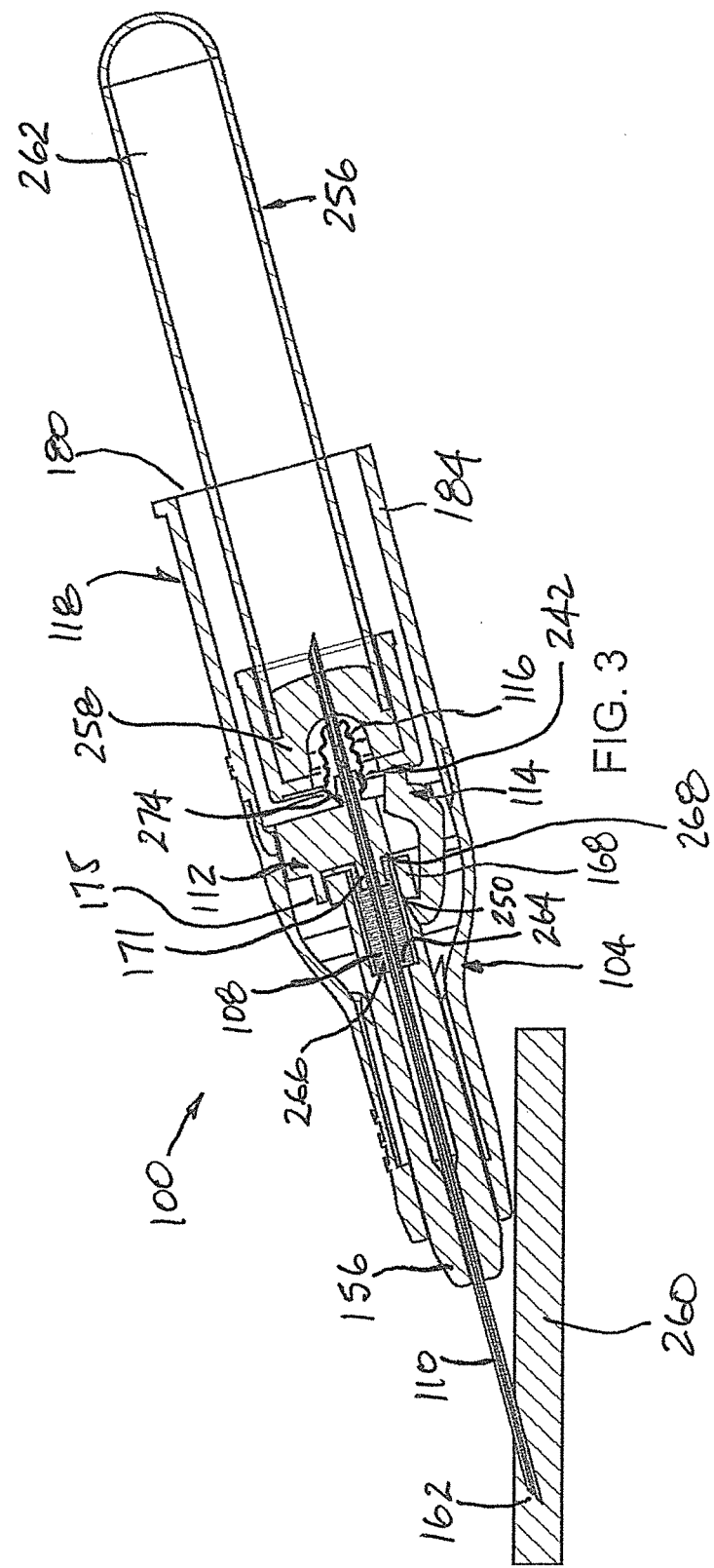
FIG. 3 shows a cross sectional side view of the assembled assembly of FIG. 1 with a blood sample vial inserted in the second housing.

Also shown in FIG. 1 is a needle 110 having a shaft with a first sharpened tip 162 and a second sharpened tip 164 projecting through the activator base 112, which has a post 171 for holding the needle and optionally for receiving bonding material to more permanently secure the needle to the activator base 112. A guide wall 175 is provided adjacent the post 171 and is spaced from the post by a gap. This allows part of the protective shield 106 is be placed therebetween during assembly, as more clearly shown in FIG. 3. The MSLA 116 is shown adjacent the second needle tip 164 and has a generally elongated rubber or elastomer body having a central lumen for receiving the second needle tip 164. The MSLA has an enlarged distal end 170 that serves to anchor the MSLA against the activator base 112. In its normal expanded state, the MSLA covers the needle tip 164. However, upon advancing the plug, such as a septum, of the vacutainer against the proximal tip 172 of the MSLA, the body of the MSLA collapses and the second sharp tip 164 is exposed to then puncture through the plug on the vacutainer to form a fluid connection between the needle and the interior of the vacutainer (FIG. 3). Upon removal of the vacutainer, the MSLA recoils and expands and the proximal tip 172 again covers the second sharp needle tip 164. The assembly may be practiced without the MSLA.

The second housing 118 is sized and shaped to receive a vacutainer through an open proximal end 180, which has a gripping flange 182. The body 184 is elongated and in the embodiment shown generally round or cylindrical with an open distal end 186 that exposes the interior surfaces 188 and the interior cavity 190. A plurality of lugs 192 can be seen through the distal opening 186 for engaging the activator base unit 112 upon assembly, as further discussed below. Optionally, a label or marking 194, such as raised molded lettering, may be incorporated on the exterior surface of the body.

Figure 2:
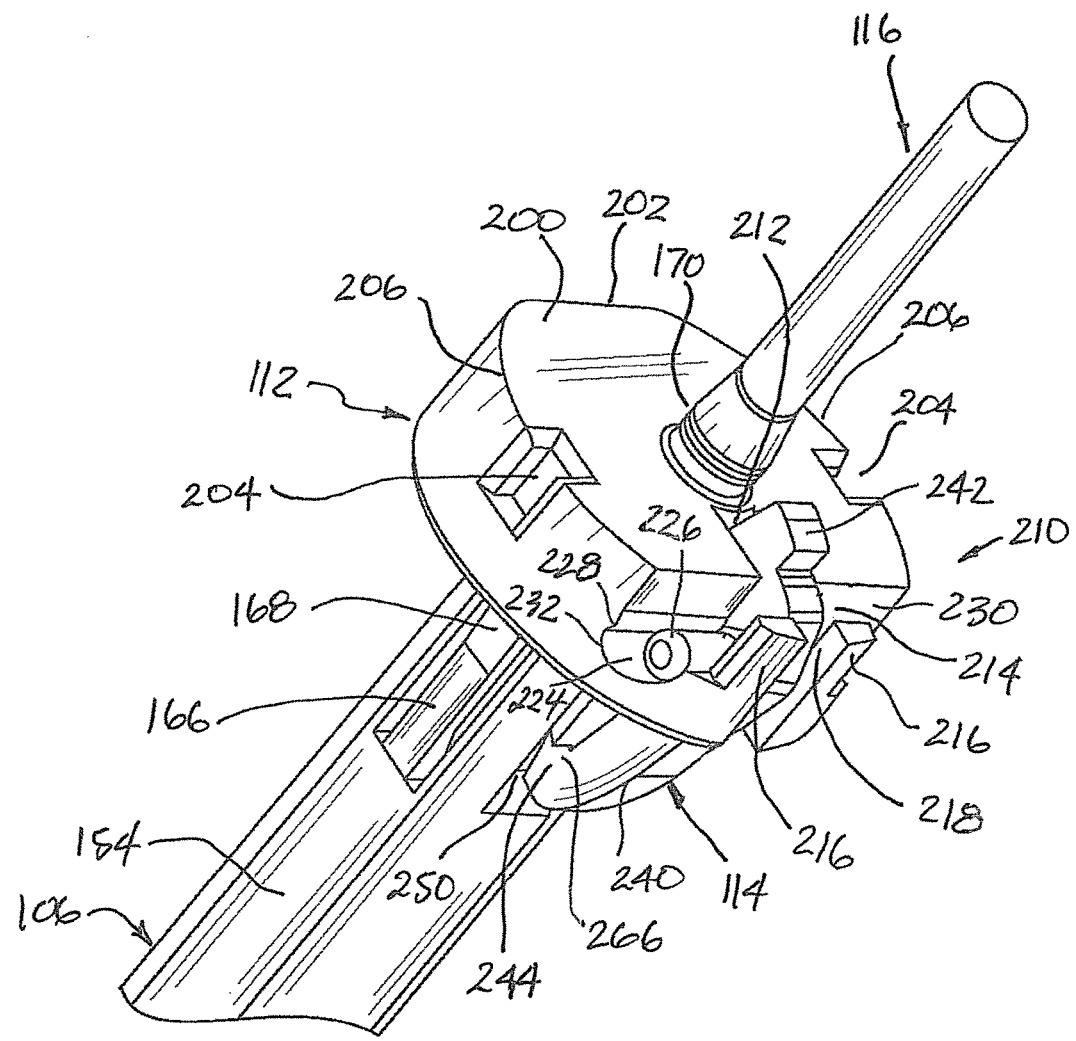
FIG. 2 shows a close up perspective view several of the components of FIG. 1 in a partially assembled state.

With reference now to FIG. 2, a partially assembled partial perspective view of several of the components of the needle assembly 100 is shown. The MSLA 116 is shown positioned over the second end of the needle 110 and over the second sharpened tip 164. The enlarged distal end 170 of the MSLA is engaged to a fitting (FIG. 5) extending out the proximal surface 200 of the activator base 112. The activator base 112 has a generally straight edge 202, two spaced apart receiving slots 204 along two curved edges 206, and a coupling area 210 for coupling to the activator lever 114. As shown, the coupling area 210 comprises a first channel 212 intersecting a second channel 214, which is defined partially by a pair of tines 216. The two tines 216 are spaced from one another and define a third channel 218 therebetween. The first channel 212 and the third channel 218 extend the entire length or thickness of the activator base 112 while the second channel 214 has a bottom wall or surface 224 for supporting the pivot pin 226 on the activator lever 114. The pivot pin 226 is retained within the second channel 214 by an interference means or a restriction surface.

To create an interference to thereby more securely retain the pin 226 of the activator lever 114 within the second channel 214, a raised bump section 228 is provided on the sidewall 230 of the second channel 214, which decreases the effective width of the second channel to a width that is slightly less than the outside diameter of the pivot pin 226. Thus, when the pin 226 snaps into the second channel 214 and past the raised bump section 228, the pin is secured within the pin receiving space 232 of the second channel 214 by a reduced section defined by the bump 228, which presents an obstacle for the pin and restricts the pin from freely popping out of the second channel 214. In one example, the two tines 216 can deflect to allow the pin 226 to snap within the pin receiving space 232.

With reference again to FIG. 1 in addition to FIG. 2, the pivot pin 226 of the activation lever 114 is mounted to the lever body 240 and is off-set from a push end 242, which may also be referred to as a leg 242. This arrangement is provided so that when the push end or leg 242 is pushed in a distal direction, such as by a plug or a septum on a vacutainer, the activator lever 114 rocks about the pin 226 and the hook end 244 comprising a hook 246 moves out of the receptacle 250 formed in the body 154 of the protective shield 106. Thus, the shield can be held by activation lever 114 and the two components separated from one another by applying an axial force to create a radial movement on the hook end of the activation lever. As further discussed below, the shield 106 is used to compress the helical spring 108 located within the cavity of the shield and the shield 106 is held with the spring 108 compressed by hooking the hook end 244 of the activation lever into the receptacle 250. Thus, the activator lever 114 is pivotably anchored to the activator base 112 and the hook end 24 is movable into the receptacle 250 of the shield 106 to engage the shield. The spring 108 can expand by removing the restraint that keeps the spring compressed. As described, this may be accomplished by pushing or advancing against the push end 242 of the activator lever 114 to move the hook 246 out of the receptacle 250.

Also shown in FIG. 2 is a leaf spring 166 (only one shown) comprising a projection 168 (see FIG. 1). When the helical spring 108 is released to move the shield 106 to the protective position, the two leaf springs 166 engage respective shoulders in the first housing section 104 thus preventing the shield from retracting to expose the needle, as further discussed below. The shield 106 is shown with a generally square cross-sectional body with rounded corners. The receptacle 250 is shown on one of the side surfaces of the generally square body. In one example, two leaf springs 166 are disposed on two opposed side surfaces of the generally square cross-sectional body. In another example, there are three leaf springs on three of the four surfaces of the generally square cross-sectional body.

FIG. 3 is a cross-sectional side view of the blood collection assembly 100 of FIG. 1 in a fully assembled state and ready for use with a vacutainer 256 inserted inside the open proximal end 180 of the second housing 118. The vacutainer 256 is inserted so that the plug or septum 258 pushes against the MSLA 116 and forces the MSLA to collapse until the second end 164 of the needle 110 pierces the septum. The enlarged end 170 of the MSLA is shown connected to a barb fitting 274. In one example, the enlarged end 170 simply snaps onto the barb fitting 274. In another example, adhesive is used to more permanently secure the MSLA to the fitting 274. As shown, the first end 162 of the needle 110 pierces the skin 260 after the vacutainer 256 is inserted into the second end 164 of the needle 110. This provides the practitioner with indication of blood flashback in the flash tube or glass tube 262 upon successful venipuncture. However, it is possible to obtain intravenous access prior to inserting the vacutainer into the second end of the needle.

As shown, the nose end 130 of the first housing 104 rests against the skin 260. Also shown is the septum 258 of the vacutainer advanced up to but does not bump into or pushed against the push end 242 of the activator lever 114. This allows the hook end 244 of the activator lever to maintain its engagement with the receptacle 160 on the shield to retain the spring 108 in the compressed state. The spring 108 is held compressed between the base 264 of the enlarged bore section 266 of the needle shield 106 and the upper surface 268 of the activator base 112 around the post 171. Blood or other biological samples can be collected in the flash tube 262 in the position shown.

Figure 4:
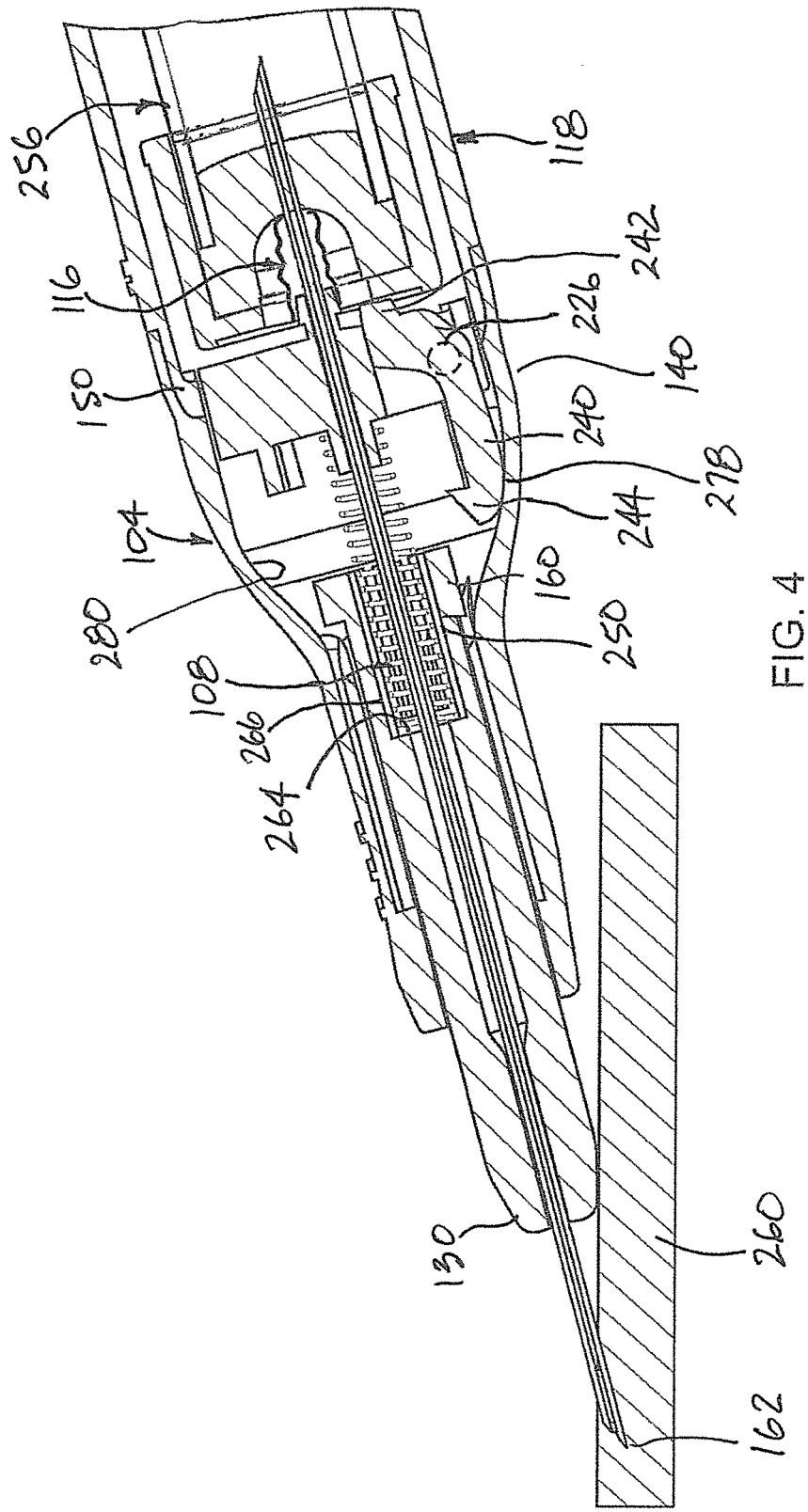
FIG. 4 shows a cross sectional side view of the assembly of FIG. 3 in an activated position.

FIG. 4 is a cross-section side view of the blood collection assembly 100 of FIG. 1 shown with the activator lever 114 actuated by further advancing the vacutainer 256 against the push end 242 of the activator lever 114 to rotate the hook end 244 away from the receptacle 250 on the safety shield 106. This removes the restraint on the spring 108 and allows it to expand, which then pushes on the base 264 of the bore 266 to advance the protective shield 106 in the distal direction. As shown, the nose section 130 of the shield 106, having been advanced in the distal direction, now touches the skin 260 and is stopped by the skin from advancing further distally over the needle tip 162. The spring 108 is therefore held in a partially compressed state by the contact between the shield and the skin. Thus, the skin 260 is understood stop the spring 108 from expanding further or freely.

Also shown in FIG. 4 is the second end 140 of the first housing 104 engaging the nose section 150 of the second housing 118. In the embodiment shown, the nose section 150 is pressed fit into the cylinder base 144 of the second end 140. The second end 140 is generally round or bell shaped to fit over the nose section 150 of the second housing section. Additionally, the enlarged second end 140 provides sufficient space for the activator lever 114 to rotate. In particular, the enlarged section end 140 is sized and shaped to provide room for the hook end 244 to move radially outwardly away from the axis defined by the needle shaft. In one example, the exterior side 278 of the hook end 244 contacts the interior surface 280 of the second end upon activation of the push end 242 by the vacutainer 256. In an alternative example, the second end 140 is sufficiently large so that a gap is provided between the interior surface and the exterior side of the hook end.

Figure 5:
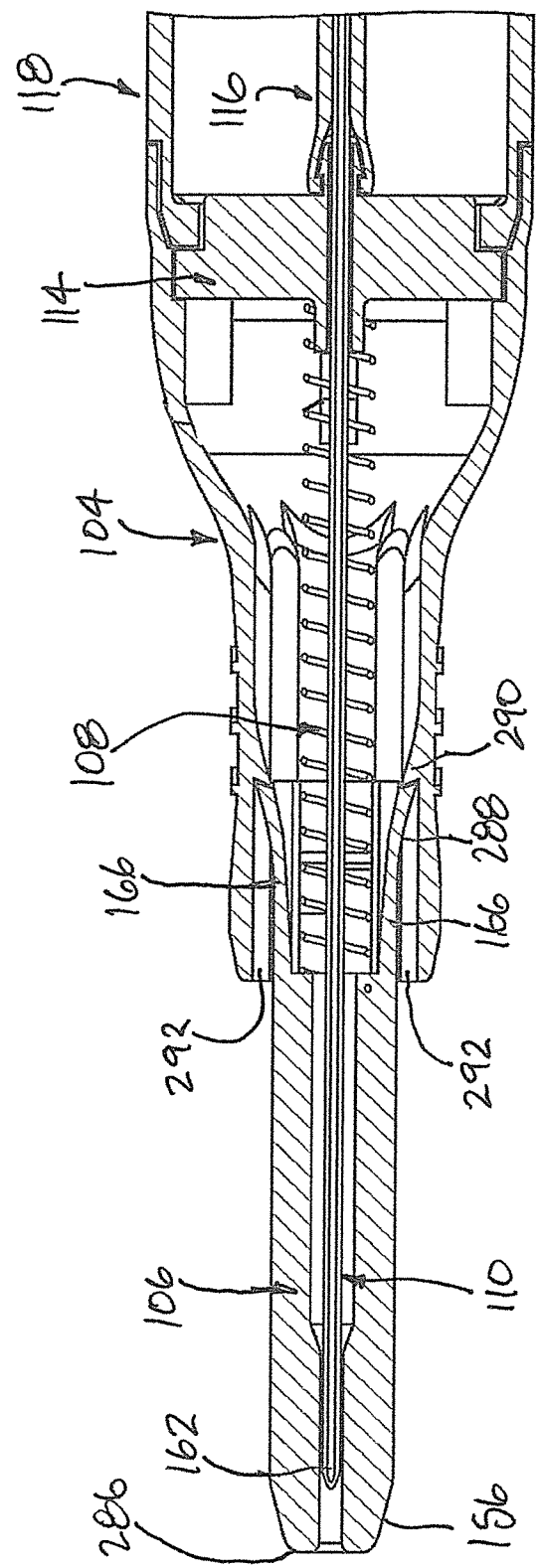
FIG. 5 shows a cross sectional side view of the assembly of FIG. 4 in a protective position.

FIG. 5 is a cross-sectional side view of the assembly 100 of FIG. 1 after withdrawal of the needle 110 from the skin 260, i.e., after retracting the needle 110 from the configuration of FIG. 4. As shown, the spring 108 is allowed to freely expand, which pushes the needle shield 106 in the distal direction so that the nose section 156 of the shield extends distal of the needle tip 162. More specifically, the distal end 286 of the nose section 156 moves distal of the needle tip 162 to cover the needle tip. The spring 108 is sized and shaped with a sufficient length, wire diameter, and spring constant to push the shield 106 in the distal direction until the proximal ends 188 of the respective leaf springs 166 on the protective shield 106 move distal of and snap into engagement with the internal shoulder 290 in the first elongated end 138 of the first housing 104. This prevents the needle shield 106 from retracting back into the first housing 104 to expose the needle tip 162. To prevent the shield 106 from moving distally and separating from the first housing section 104, the channels 292 having the leaf springs 166 disposed therein may have a tapered distal end or a notch to prevent the projection on the leaf spring from moving there past. A separate leaf spring or projection may be provided that are separate from the proximally located leaf springs 166 to stop the shield from unintentionally separating from the first housing section 104. In still another example, the elongated end 138 of the first housing section 104 has a projection that projects into the receptacle 250 on the shield 106 to prevent the shield from separating from the first housing 104. Other means for preventing complete separation of the protective shield 106 from the first housing is contemplated.

FIG. 5 is shown with the vacutainer 256 removed from the second end 164 of the needle. Upon doing so, the MSLA 116 is allowed to expand and returns to its less compressed or distorted state. Although not shown, the MSLA expands so that the second tip 164 is covered by the MSLA. In another example, before the blood collection assembly 100 is removed from the skin, i.e., from the FIG. 4 position, the vacutainer is removed and a new vacutainer placed into fluid communication with the needle 110 to take additional samples. In the protective position shown in FIG. 5, the first needle tip 162 is covered by the protective shield 106 and is prevented from potential re-use. The shield is held fixed in the proximal and distal direction in the shield protective position.

As described, the blood collection assembly is understood to include a housing for receiving a vacutainer and puncturing the plug on the glass tube with a needle having a first tip and a second tip. The assembly is further understood to include an activator unit for activating a needle shield to cover the first tip following use. A spring is optionally used to propel the shield to cover the first tip. Alternatively, the protective shield is manually moved in a distal direction by the user to cover the first tip.

To activate the needle shield with the activator or activating unit, the vacutainer is advanced against the activator unit to release the shield, which is then free to move in a distal direction by the spring, or by the user if a spring is not incorporated. In an alternative embodiment, a lever or button is provided so that the activator unit is triggered by a user's finger. In an example, the shield is held by the skin of a patient during cannulation and does not cover the first tip after the activator unit is activated. However, the vacutainer can advance against the activator unit to activate it when the needle is not stuck to the patient so that the shield immediately moves in the distal direction to cover the first tip.

The activator unit is understood to include a rotatable component. As described, the activator unit includes an activator lever that rotates about a pivoting axis. Two pins located on a body of the activator lever are provided to enable the activator lever to rotate. The activator lever further has an offset push end that allows the opposite end of the body to rotate along an arc. This angular movement is used to separate a hook end on the activator lever from the shield, which then frees the shield for movement in the distal direction to cover the first tip.

The present disclosure is also understood to include methods for manufacturing the blood collection assembly and for using the blood collection assembly.

Figure 6:
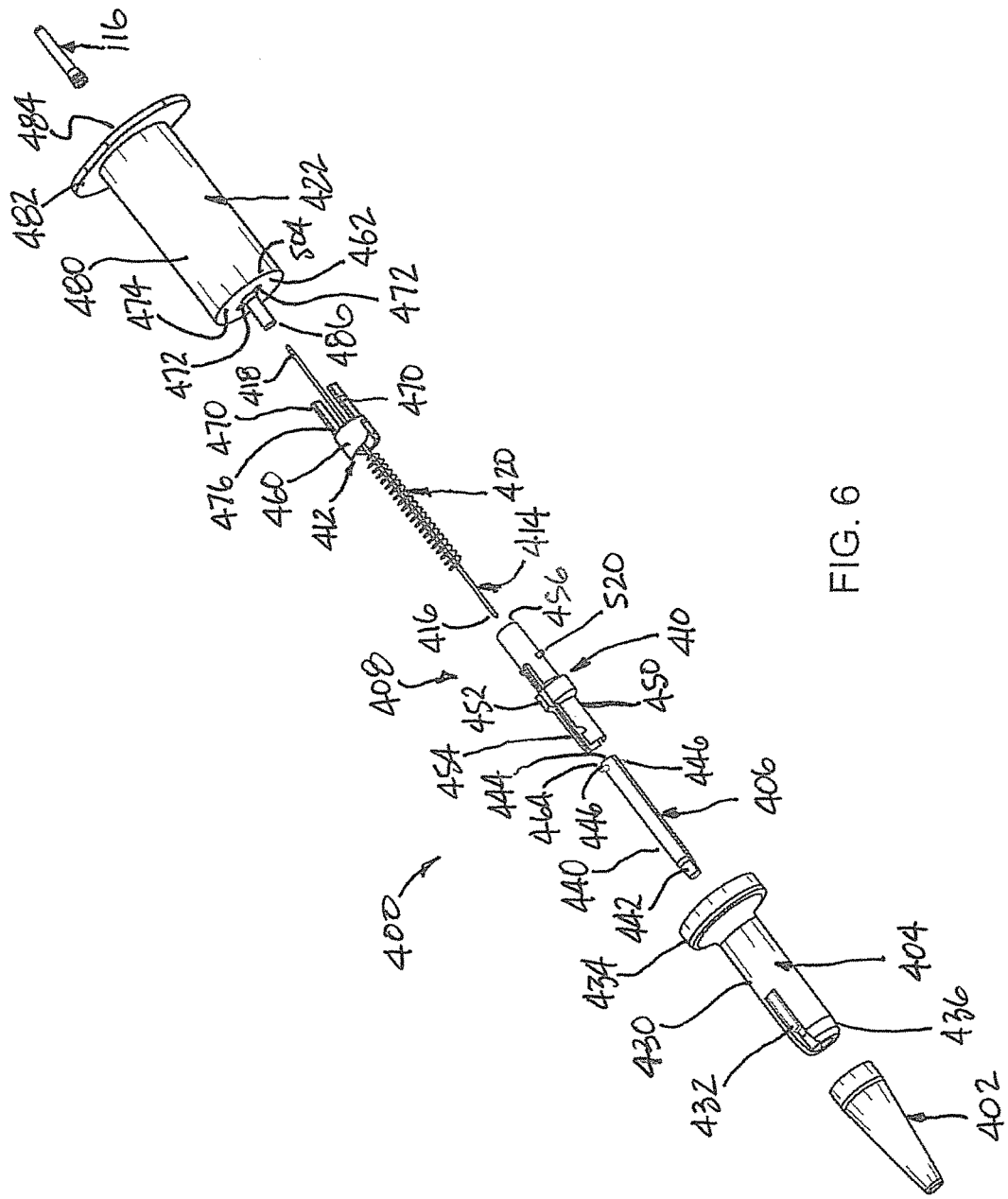
FIG. 6 shows an exploded perspective view of a safety needle blood sampling assembly in accordance to further aspects of the present disclosure.

FIGS. 6-8 show an alternative embodiment of a blood collection assembly provided in accordance with aspects of the present disclosure, which is generally designated 400. The assembly 400 comprises a removable cap 402, a first housing 404, a protective shield 406, an activator unit 408 comprising an activator base 410 and an activator lever 412, a needle 414 having a first needle tip 416 and a second needle tip 418, a helical spring 420, a second housing 422, and a multi-sample Luer adaptor (MSLA) 116. Thus, the blood collection assembly 400 of FIGS. 6-8 share many similar components as the assembly 100 of FIGS. 1-5 with the following exceptions.

Viewing from the left side of FIG. 6 to the right, the removable cap 402 is configured to fit around the body 430 of the first housing 404 to temporarily cover the needle 414 during storage and shipping of the blood collection assembly 400. The cap 402 is configured to be removed and disposed of prior to using the blood collection assembly.

The first housing 404 has an elongated body or first end 430 comprising at least two leaf springs 432 formed by at least two cut-outs on either side of each leaf spring and a clearance along the tip of the leaf spring, on the end opposite where the leaf spring is attached to the body. The housing 404 further comprises an enlarged second end 434 for press fitting around the second housing 422, as shown in FIGS. 7 and 8. While the first end 430 is generally elongated and can have a generally constant outside diameter with varying diameters contemplated, a tapered nose section 436 is incorporated at a distal end to facilitate assembly with the removable cap 402. A bore extends a lengthwise axis of the first housing 404 and or more labels or text messages may be applied to the exterior surface of the body 430 for aesthetic appeal or information purposes.

The protective shield 406 comprises a body 440 defining an elongated cylinder having a tapered nose section 442, an open proximal end 444, and two radially extending stubs or pins 446. A bore extends through the lengthwise axis of the shield for sliding movement over and relative to the needle 414 to shield the needle in a protective position, as further discussed below. The shield 406 is configured to slide within the activator base 410 and the first housing 404 to shield the needle. The body is generally round with other shaped bodies contemplated. Further, while two stubs 446 are shown, the shield may be practiced with just one stub or more than two.

Figure 14:
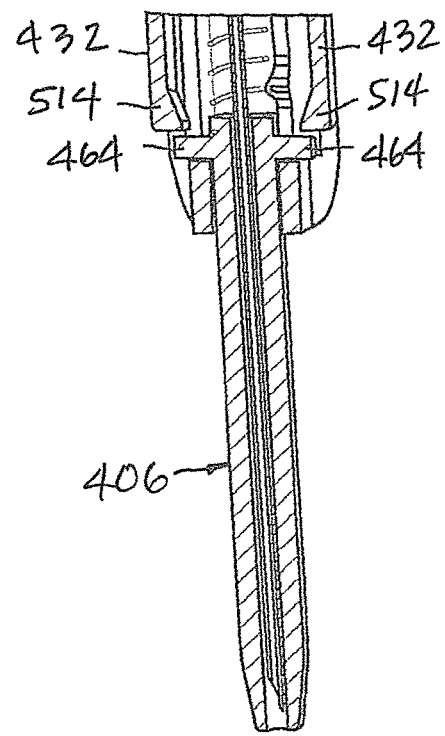
FIG. 14 shows the embodiment of FIG. 6 in a protected position.

The activator base 410 is configured to temporarily hold the shield 406 in an initial pre-use configuration in which the shield partially or completely cover the needle, as shown in FIGS. 7 and 8. Upon activation, as further discussed below, the activator base 410 moves, such as to rotate, to free the shield 406 to move and to eventually cover the first end 416 of the needle 414 following use, such as shown in FIG. 14. The activator base 410 comprises a body 450 comprising an enlarged mid-section 452, two channels 454 running lengthwise of the axis of the activator base 410 for at least part of the activator base, and an open proximal end 456 that opens into an internal bore for receiving the needle 414. The length of the channels 454 can be selected to control the amount of travel of the stubs 446 on the protective shield 406. The enlarged mid-section 452 has an outside dimension that is sized and shaped to fit within the first housing 404 and to act as a guide or bearing with the interior surface of the first housing so as to steady the activator base 410 within the first housing when the assembly is activated. As shown in FIGS. 7 and 8, the enlarged mid-section fits within the bore of the first housing with reduced clearance. The activator base 410 further comprises a pair of stubs 520 for cooperating with the activator lever 412, as further discussed below. In other examples, only one stub or more than two may be used.

The spring 420, like the spring 108 of FIG. 1, is configured to propel the shield 406 over the needle to cover the needle tip 416 in a protective position. In the assembled state, the spring 420 is positioned within the cylindrical end 460 of the activator lever 412 and is compressed by the distal exterior surface 462 of the second housing 422 and the end wall 464 of the open proximal end 444 of the protective shield. When permitted to expand, the spring 420 pushes the end wall 464 of the protective shield 406 in the distal direction to cover the needle tip 416.

The activator lever 412 has a pair of leg extensions 470 extending from the cylinder end 460. The two legs are spaced from one another and have a gap therebetween for accommodating the needle. The two leg extensions 470 are configured to project into corresponding bores 472 in the end wall 474 of the second housing 422. In one example, the two leg extensions 470 extend all the way into the second housing so that the end wall 474 contacts the end wall surface 476 of the cylinder end 460. In another example, the leg extensions 470 only extend partially into the corresponding bores 472 on the end wall 474 and a gap is provided between the end wall 474 and the end wall surface 476.

The second housing 422 has a body 480 that is sized and shaped to receive a vacutainer through the open proximal end 484. A flange 482 is provided at the open proximal end 484 and a post 486 at the distal end on the end wall 474 to retain the needle 414. When assembled, the needle shaft projects through the bore provided in the post 486 and is held thereto using conventional means. Part of the needle shaft with the second tip 418 projects into the hollow interior space of the second housing and is covered by the MSLA 116.

With reference now to FIGS. 7 and 8, the blood collection assembly of FIG. 6 is shown in an assembled state and shown with two different cross-sectional side views. In particular, FIG. 7 shows the assembly in a ready to use position and along a plane that shows the two leg extensions 470 on the activator lever 420. FIG. 8 shows the assembly of FIG. 7 from a different viewing plane, rotated 90 degrees. With reference again to FIG. 7, the two leg extensions 470 on the activator lever 412 are inserted into the bores 472 on the end wall 474 of the second housing 422. A clearance is provided between the leg extensions and bores 472 to allow the leg extensions to move along the axial direction of the needle shaft, such as when pushed by the vacutainer 256. A projection 490 is provided on each leg extension to deter the legs from completely separating from the bores 472 in the distal direction unless purposely pushed by the vacutainer 256 in a secondary, second mode, or alternative activation process, as further discussed below. Thus, the activator lever 412 is understood to be movable in the axial direction along the shaft but not rotationally any significant amount, if at all, relative to the axis of the needle due to the physical constraints between the leg extensions 470 and the bores 472.

The vacutainer 256 is shown inserted into the interior space of the second housing 422 with the plug or septum 258 pushed up against and collapsing the MSLA 116 so that the needle 414 punctures the plug. In practice, the vacutainer may optionally be inserted into the second housing 422 after successful cannulation of the patient or subject. However, unless the shield 406 is to be activated using the alternative activation, the plug 258 may touch but does not materially advance the two leg extensions 470 to the point in which the two projections 490 on the two legs are pushed distally through the two bores 472. Preferably, the plug 258 is punctured by the needle 414 but is otherwise spaced from the two leg extensions 470 by a gap. In some embodiments, the septum can touch and even advance the two leg extensions in the distal direction a small distance without activating the shield 406. In one example, the assembly is practiced without the MSLA.

With further reference to FIG. 7, the activator base 410 is positioned inside the bore of the cylinder end 460 of the activator lever 412, which has a shoulder for limiting the extent of insertion of the activator base 410 into the cylinder end. The activator base 410 is rotatable relative to the needle and the activator lever 412 but not translatable any significant amount due to the constraint at both ends of the activator base. The spring 420 is located in the bore of the activator base 410, in the annular space between the needle 414 and the activator base 410. The protective shield 406 is placed over the needle with the two stubs 446 at the proximal end of the shield aligned to the two channels 454 on the activator base 410. The protective shield 406 is inserted until the two stubs 446 can be rotated and engage the two catchments 494 formed along the two channels 454. Each catchment 494 has a flat section 496 and a tapered section 496. The stubs are rotated into the respective catchments 494 and are pushed against the respective flat sections 496 by the spring 420, which is partially compressed by the proximal end of the protective shield 406. In the ready to use position shown, the first needle tip 416 projects out of distal end 500 of the needle shield 406 to enable cannulation and activation, as further discussed below.

As shown, the first housing 404 is positioned over or around the activator base 410, the spring 420, and the activator lever 412. The second end 434 of the first housing 404 engages the distal shoulder 504 of the second housing 422 to secure the various components, including the shield 406, to the second housing 422. The internal bore base 506 of the first housing 404 maintains contact with the distal end of the activator base 410 to ensure adequate loading on the various components between the base 506 and the end wall 574 of the second housing 422.

With reference now to FIG. 8, the blood collection assembly is shown rotated 90 degrees about the axis of the needle from the plane of FIG. 7. As shown, the needle shield 406 comprises a fin 510 extending from the nose section 442 and running or extending to a proximal position near or adjacent the axial position of the two stubs 446. In one example, two fins 510 are provided at equally spaced apart positions on the protective shield 406. The fins are generally straight and parallel to the needle. The fins 510, which may also be referred to as tracks, are configured to slide along corresponding grooves or channels formed on the interior of the tapered nose section 442 of the first housing 404, similar to a tongue and groove arrangement. The fins 510 and the corresponding grooves allow the shield 406 to move along the axial direction of the needle shaft but not rotatable about the axis of the shaft due to their inter-engagement. This allows the shield to telescopically move within the first housing but not rotate. Thus, between the shield 406, the activator base 410, and the activator lever 412, only the activator base 410 is permitted to move a substantial or intended angular rotation to activate the shield 406, as further discussed below.

With further reference to FIG. 8, a pair of leaf springs 432 are provided with the first housing 404, which may be formed by providing at least three distinct cut-outs on the body 430 of the first housing 404 along three sides of each leaf spring and allowing the leaf spring to deflect along the fourth side. Each leaf spring has a projection 514 comprising a flat surface 516 and a tapered surface 518. The projection 514, such as the tapered surface 518, acts as a cam to be pushed by the stub 446 on the protective shield 406 and as a stop, such as the flat surface 516, to support the stub 446 and prevent the shield 406 from retracting upon activation to cover the needle, as further discussed below.

Like the protective shield 406, the activator base 410 has a pair of stubs 520 near its proximal end, which is understood to be the end that is closer to the practitioner than to the patient and is generally opposite the distal end. The stubs 520 are equally spaced on the activator base but can be positioned differently around the body. In the assembly initial or ready to use position shown in FIG. 8, the stubs 520 are located in corresponding catchments 522 formed on the cylinder end 460 of the activator lever 412. Each catchment 522 comprises a channel 524 and an inlet or opening 526 to the channel. At least one tapered edge 528 is provided at the inlet to the channel. As further discussed below, the activator lever 412 is configured to advance in the distal direction by a vacutainer in a secondary or alternative activation step and the two tapered edges 528 of the two catchments 522 ride against the respective stubs 520 on the activator base 410. Since the activator lever 412 is configured to primarily move in the axial direction and the activator base 410 is configured to primarily rotate about the needle, the distal movement of the activator lever 412 causes the activator base 410 to rotate. Specifically, the stubs 520 move, such as rotate, along the tapered edges 528 of the two respective catchments 522, which produce a radial force and an axial force. Concurrently with this movement, the stubs 446 on the protective shield 406 (FIG. 7) move out of the catchments on the activator base 410 and into the elongated channels 454. The stubs 446 can now freely travel within the channels 454 until trapped by the leaf springs 432. The stubs and catchments combination may be referred to as a trigger device. Thus, the present assembly has a first trigger device 570, which is the combination stubs 446 and catchments 494 on the shield 406 and the activator base 416 (FIG. 7), and a second trigger device 572, which is the combination stubs 520 and catchments 522 on the activator base 410 and the activator lever 412 (FIG. 8). As used with the trigger devices, an action of the stubs or catchments causes the other corresponding components to either rotate or move in an axial direction.

Thus, an aspect of the present disclosure is understood to include two spaced apart trigger devices 570, 572. In one example, activation of the second trigger device 572 causes the first trigger device 570 to activate. However, activation of the first trigger device 570 does not fully activate the second trigger device 572, as further discussed below. In the case of the first trigger device 570, its activation only causes the stubs of the activator base to rotate but not the corresponding catchments, as further discussed below.

With reference now to FIGS. 9-11, the second mode or alternative mode of activation is shown in a sequence of drawings. With reference first to FIG. 9, the activator base 410 is shown rotated so that the two stubs 446 on the protective shield 406 are no longer located in the corresponding catchments 494 on the activator base. As discussed above, this may be practiced by advancing the vacutainer 256 in the distal direction so that the septum 258 advances against the two leg extensions 470, which causes the cylinder end 460 of the activator lever 412 to advance against the stubs 520 on the activator base 410, which causes the activator base 410 to rotate.

FIG. 10 shows the assembly of FIG. 9 rotated 90 degrees to show the assembly from a different viewing angle. As shown, the channels 524 on the cylinder end 460 of the activator lever 412 have advanced against the stubs 520 (only one shown) on the activator base 410. The projections 490 (only one shown) on the leg extensions 470 are shown located distally of the bores 472 on the end wall 474 of the second housing 422 due to the advancement of the septum 258 against the leg extensions 470.

Although the shield 406 shown in FIG. 10 is urged by the spring 420 when the stubs 446 separate from their corresponding catchments 494, the spring 420 is near its full travel and does not have sufficient spring force to push the two stubs 446 pass the projections 514 on the two leaf springs 432 located on the first housing 404. After the activator base 410 is activated by the activator lever 412 and the shield 406 is free to travel further into the activator base from the position shown, the assembly 400 is ready for cannulation. In practice, the needle tip 416 is pushed into the skin and the skin pushes against the nose end of the shield 406. As the needle 414 penetrates the skin, the skin further pushes on the shield to move the shield deeper into the activator base 410, which resembles the shield position shown in FIG. 13. Blood is then collected in the glass tube 262 of the vacutainer upon successful cannulation. Additional samples may be taken by removing the vacutainer with the sample and sequentially inserting new vacutainers into the second end of the needle to obtain subsequent samples.

After a desired number of samples are taken, the needle is removed from the patient. By retracting the assembly away from the patient and particularly the skin, the restraint on the shield 406 is released and the spring 420, from a compressed position, is allowed to quickly expand at about the same speed as the retraction of the needle from the skin. As shown in FIG. 11, this expansion is sufficient to force the two stubs 446 on the shield 406 to move past the projections 514 on the two leaf springs 432 and be captured by the flat sections 516 of the two projections. Concurrently therewith, the distal end 500 of the shield moves past the needle tip 416 to cover the needle tip from accidental contact therewith, which is more clearly shown in cross-section in FIG. 14.

With reference now to FIG. 12, the assembly 400 is shown activated in accordance to a first mode or primary mode of activation. Although the assembly is shown without a vacutainer, one is assumed to be inserted into the second end of the needle and be in fluid communication with the needle. However, the septum on the vacutainer does not advance against the two leg extensions 470 to distally move the activator lever 412 as discussed above with reference to FIGS. 9 and 10 to free the stubs 464 from the catchments 494 of the first trigger device 470. Instead, from the perspective of FIG. 7 and then FIG. 12, the needle can advance against the skin to obtain venous blood samples. Upon the skin contacting the distal end 500 of the shield as the needle penetrates the skin, the shield is pushed in the proximal direction and causes the two stubs 464 to move against the respective tapered sections 498 of the corresponding catchments 494. Since the activator base 410 is freely rotatable, this contact imparts a lateral force and causes the activator base to rotate to move the catchments 494 away from the two stubs 446. This is shown in FIG. 12. The needle can then further penetrate deeper into the skin to obtain venous access.

Figure 13:
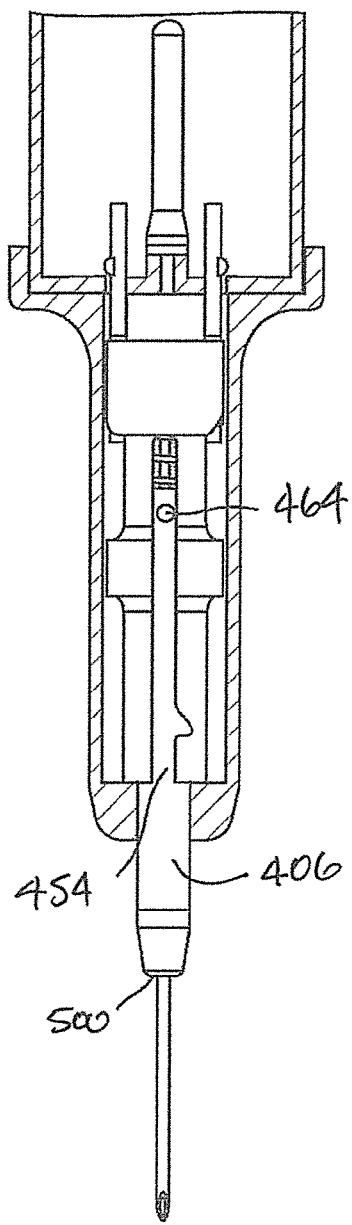
FIG. 13 shows the embodiment of FIG. 6 in a shield compressed position.

FIG. 13 shows the shield 406 pushed in the proximal direction into the activator base 410, such as by the skin pushing against the distal end 500 of the shield during cannulation. When the spring is allowed to release, such as by removing the restraint on the shield, the spring expands and moves the shield 406 in the distal direction to cover the needle tip, such as that shown in FIG. 14. During the spring expansion step, the stubs 446 on the shield are moved distal of the projections 514 and captured by the flat surfaces 516 on the two projections. This prevents the shield 406 from telescoping back into the first housing 404 to expose the needle tip.

The present disclosure is also understood to include methods for manufacturing the blood collection assembly and for using the blood collection assembly 400.

Although limited embodiments of the safety needle blood sampling device assemblies and their components have been specifically described and illustrated herein, many modifications and variations will be apparent to those skilled in the art. For example, the various protective shields may incorporate translucent materials allowing a user to view the needle after the needle shield is released, etc. Furthermore, it is understood and contemplated that features specifically discussed for one safety needle blood sampling device embodiment may be adopted for inclusion with another safety needle blood sampling device embodiment, provided the functions are compatible. For example, a hollow seat for receiving a vial in an activator may be used in another embodiment shown with just the ring and leg elements. Another example includes elements that allow a user to detect flashback. Accordingly, it is to be understood that the safety needle blood sampling device assemblies and their components constructed according to principles of the disclosed devices, systems, and methods may be embodied other than as specifically described herein. The disclosure is also defined in the following claims.

What is claimed is:

1. A safety needle blood sampling device comprising:
    a housing comprising a first housing section having a first open end and a second open end attached to a first end of a second housing section, which has an open second end for receiving a sampling vial, the housing comprising an interior space;
    a needle passing through the housing and having a needle shaft extending at least partially in the first housing section for cannulation and into the second housing section for connection to a sampling vial;
    an activator unit disposed in the interior space of the housing, said activator unit comprising:
        an activator base comprising a base body having a distal end surface and a proximal end surface and a channel extending between the distal and proximal end surfaces of the base body; and
        an activator lever and wherein the activator lever comprises at least one leg located in the second housing section for contacting a sampling vial when the sampling vial is located in the second housing section and wherein the needle shaft passes through the activator base; and
    a protective shield having a body defining a bore, said body defining the bore of the protective shield having a first end and a second end and being urged by a helical spring disposed at least partially inside the first housing section, said protective shield comprising a tapered nose section at the first end;
    wherein prior to placement of a sampling vial in connection with the second housing section, the protective shield is engaged by the activator base or the activator lever to maintain the spring in a compressed state in a ready to use position with a first needle tip exposed distal of the protective shield; and
    wherein a section of the base body of the activator base is located entirely between the first open end and the second open end of the first housing section.

2. The safety needle blood sampling device of claim 1, wherein the first housing section is snap fit around an outside surface of the second housing section.

3. The safety needle blood sampling device of claim 1, wherein the activator lever comprises a pivotable pin attached to a channel formed in the activator base and the at least one leg defines a push end.

4. The safety needle blood sampling device of claim 3, wherein the activator lever has a hook end that hooks into a receptacle on the protective shield in the ready to use position.

5. The safety needle blood sampling device of claim 1, wherein the channel of the activation base extends parallel to the needle.

6. The safety needle blood sampling device of claim 1, wherein the protective shield comprises a stub extending laterally of a lengthwise axis of the protective shield and wherein the stub engages a catchment on the activator base in the ready to use position.

7. The safety needle blood sampling device of claim 1, wherein the activator lever has a cylinder end comprising a catchment for engaging a stub on the activator base.

8. The safety needle blood sampling device of claim 5, wherein the channel comprises a catchment comprising a slanted section for rotating the activation base when pushed by a stub.

9. The safety needle blood sampling device of claim 5, further comprising a catchment with a slanted section located within the channel and proximal of an end opening.

10. The safety needle blood sampling device of claim 1, wherein the activator base comprises an enlarged mid-section that is sized and shaped to fit within an interior of the first housing section to act as a guide or bearing with an interior surface of the first housing section.

11. The safety needle blood sampling device of claim 1, wherein the activator lever has a cylinder end for receiving at least part of the activator base.

12. The safety needle blood sampling device of claim 11, wherein the cylinder end comprises a channel comprising a catchment.

13. The safety needle blood sampling device of claim 11, wherein the at least one leg is a first leg and activator lever comprises a second leg spaced from the first leg, and both the first and second legs extend from the cylinder end.

* * * * *